United States Patent [19]

Bovenberg et al.

[11] Patent Number: 5,726,032
[45] Date of Patent: Mar. 10, 1998

[54] PROCESS FOR THE EFFICIENT PRODUCTION OF 7-ADCA VIA 2-(CARBOXYETHYLTHIO)ACETYL-7-ADCA AND 3-(CARBOXYMETHYLTHIO) PROPIONYL-7-ADCA

[75] Inventors: Roelof Ary Lans Bovenberg, Rotterdam; Bertus Pieter Koekman, Schipluiden; Andreas Hoekema, Oegstgeest; Jan Metske Van Der Laan, Breda; Jan Verweij; Erik De Vroom, both of Leiden, all of Netherlands

[73] Assignee: Gist-Brocades B.V., Netherlands

[21] Appl. No.: 592,411

[22] PCT Filed: Jul. 29, 1994

[86] PCT No.: PCT/EP94/02543

§ 371 Date: Apr. 4, 1996

§ 102(e) Date: Apr. 4, 1996

[87] PCT Pub. No.: WO95/04148

PCT Pub. Date: Feb. 9, 1995

[30] Foreign Application Priority Data

Jul. 30, 1993 [EP] European Pat. Off. ............ 93202259
Dec. 24, 1993 [EP] European Pat. Off. ............ 93203696

[51] Int. Cl.$^6$ .................... C12P 35/00; C12P 35/02; C12P 35/06; C12N 1/15

[52] U.S. Cl. ................... 435/51; 435/47; 435/49; 435/172.3; 435/254.5

[58] Field of Search ................. 435/47, 49, 51, 435/320.1, 254.5, 172.3; 556/23.2

[56] References Cited

FOREIGN PATENT DOCUMENTS 0532341  3/1993  European Pat. Off. .
0540210  5/1993  European Pat. Off. .

OTHER PUBLICATIONS

De Hoop et al., Biochem. J. 286:657–669 (1992).
Müller et al., Biochemica et Biophysica Acta 1116:210–213 (1992).
Barredo et al., Gene 83:291–300 (1989).
Diez et al., Mol. Gen. Genet. 218:572–576 (1989).

Primary Examiner—George C. Elliott
Assistant Examiner—Johnny F. Railey, II
Attorney, Agent, or Firm—Bierman, Muserlian and Lucas LLP

[57] ABSTRACT

An overall efficient process for the preparation and recovery of 7-aminodesacetoxycephalosporanic acid (7-ADCA) via 2-(carboxyethylthio)acetyl- and 3-(carboxymethylthio)propionyl-7-ADCA, using a *Penicillium chrysogenum* transformant strain expressing expandase in conjunction with acyltransferase, is provided.

4 Claims, 9 Drawing Sheets

```
478  CTGCGCCTGCGCTACTTCCCCGAGGTGCCCGAGGATCGCGTGGCCGAGGAGCAGCCGCTG
481  CTGCGCCTGCGCTACTTCCCCGAGGTGCCCGAGGATCGCGTGGCCGAGGAGCAGCCGCTG

538  CGGATGGCCCCGCACTACGACCTCTGATCGTCACCCTGATCCACCAGACCCCTTGCGCG
541  CGGATGGCCCCGCACTACGACCTCTGATCGTCACCCTGATCCACCAGACCCCCTTGCGCG

598  AACGGGTTCGTCAGCCTGCAGGTCGAGGTGGACGGGTCCTATGTGGACATCCCGGCGCAG
601  AACGGGTTCGTCAGCCTGCAGGTCGAGGTGGACGGGTCCTATGTGGACATCCCGGCGCAG

658  CCGGGGCGGGTGCTGTGTTCTGCGGCGGTGGCCGACGCTGGTGGCCGACGGCGCGATC
661  CCGGGGCGGGTGCTGTGTTCTGCGGCGGTGGCCGACGCTGGTGGCCGACGGCGCGATC

718  AAGGCGCCCAAGCACCACGTGGCCGGCGCCCGGCGCCGGACAAGCGGGTGGGCAGCAGCCGC
721  AAGGCGCCCAAGCACCACGTGGCCGGCGCCCGGCGCCGGACAAGCGGGTGGGCAGCAGCCGC

778  ACCTCCAGCGTGTTCTTCCTGCGCCCCAACGGGGACTTCCGCTTCCGCTTCCGGTGCCCGGGCC
781  ACCTCCAGCGTGTTCTTCCTGCGCCCCAACGGGGACTTCCGCTTCCGCTTCCGGTGCCCGGGCC

838  AGGGAGTGCGGGTTCGACGTCAGCATCCCGGCCGAGACATCCCGGCCGAGACCGCCACCTTCGACGACTGGATC
841  AGGGAGTGCGGGTTCGACGTCAGCATCCCGGCCGAGACATCCCGGCCGAGACCGCCACCTTCGACGACTGGATC

898  GGCGGCAACTACATCAACATCCGGAAGACCCGCCGCCCGG                          939
901  GGCGGCAACTACATCAACATCCGGAAGACCCGCCGCCGCCCGG                       942

Matches = 937    Length = 942    Matches/length = 99.5 percent

FIG. 8A
```

```
  1  ATGACGGACGCGACCGTGCCGACCTTCGATCTGGCCGAGCTGCCTGAGGGCTTGCACCAG
  1  ATGACGGACGCGACCGTGCCGACCTTCGATCTGGCCGAGCTGCCTGAGGGCTTGCACCAG

61  GAGGAGTTCCGCCACTGCCTGCGCGCCGAGAAGGGCGTGTTCTACCTCAAGGGCACCGGGCT
 61  GAGGAGTTCCGCCACTGCCTGCGCGCCGAGAAGGGCGTGTTCTACCTCAAGGGCACCGGGCTG
                                                                *
120  C G CCGAGGGCGACCACGCCTCGGCGCCGGGAGATCGCGGTGGACTTCTTCGACCACGGC
121  CCGGCCGAGGGCGACCACGCCTCGGGCGCCGGGAGATCGCGGTGGACTTCTTCGACCACGGC
     * *
178  ACCGAGGCCCGAGAAGAAGGCGGTGATGACGCCGATCACGAACACCGGCAAGTACACCGACTACTCG
181  ACCGAGGCCCGAGAAGAAGGCGGTGATGACGCCGATCACGAACACCGGCAAGTACACCGACTACTCG

238  GGGCTGGAGTCCGAGAGAGCACCGGCAGATCACCACGAACACCGGCAAGTACACCGACTACTCG
241  GGGCTGGAGTCCGAGAGAGCACCGGCAGATCACCACGAACACCGGCAAGTACACCGACTACTCG

298  ATGTCGTACTCGATGGGCACCGGGACAACCTGTTCCCCAGCGCCGAGTTCGAGAAGGCG
301  ATGTCGTACTCGATGGGCACCGGGACAACCTGTTCCCCAGCGCCGAGTTCGAGAAGGCG

358  TGGGAGGACTACTTCGCGGCGGATGTACCGCGCTTCGCAGGACGTCGCGCGGCAGGTGCTG
361  TGGGAGGACTACTTCGCGGCGGATGTACCGCGCTTCGCAGGACGTCGCGCGGCAGGTGCTG

418  ACCTCGGTCGGCGCGGAACCCGAGGTTCGGCATGACGCCTTCCTCGACTGCGAACCCCTG
421  ACCTCGGTCGGCGCGGAACCCGAGGTTCGGCATGACGCCTTCCTCGACTGCGAACCCCTG
```

FIG. 8B

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: oligonucleotide 1

( x i ) SEQUENCE DESCRIPTION: SEQ ID NO: 1:

```
GCTGAAGGAG  CTGAGCATAT  GACGGACGCG  ACCGTGCCGA  CC                    4 2
```

( 2 ) INFORMATION FOR SEQ ID NO: 2:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: oligonucleotide 2

( x i ) SEQUENCE DESCRIPTION: SEQ ID NO: 2:

```
CCCGGGTCTA  GATCTAGATC  ACCGGGCGGC  GGCGGTCTTC  CGGATGTT              4 8
```

( 2 ) INFORMATION FOR SEQ ID NO: 3:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: oligonucleotide 3

( x i ) SEQUENCE DESCRIPTION: SEQ ID NO: 3:

GATCAGTGAG AGTTGCATAT GGACACGACG GTGCCCACCT TCAGCCTG    48

( 2 ) INFORMATION FOR SEQ ID NO: 4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: oligonucleotide 4

( x i ) SEQUENCE DESCRIPTION: SEQ ID NO: 4:

CCCGGGTCTA GATCTAGACT ATGCCTTGGA TGTGCGGCGG ATGTT    45

( 2 ) INFORMATION FOR SEQ ID NO: 5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: oligonucleotide 5

( x i ) SEQUENCE DESCRIPTION: SEQ ID NO: 5:

GAGCTCTGTG AATTCACAGT GACCGGTGAC TCTTTC    36

( 2 ) INFORMATION FOR SEQ ID NO: 6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: oligonucleotide 6

( x i ) SEQUENCE DESCRIPTION: SEQ ID NO: 6:

GGGAGCCATA TGGATGTCTG CTCAAGCGGG GTAGCT    36

( 2 ) INFORMATION FOR SEQ ID NO: 7:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: oligonucleotide 7

( x i ) SEQUENCE DESCRIPTION: SEQ ID NO: 7:

```
AGAACGGATT AGTTAGTCTG AATTCAACAA GAACGGCCAG AC                42
```

( 2 ) INFORMATION FOR SEQ ID NO: 8:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: oligonucleotide 8

( x i ) SEQUENCE DESCRIPTION: SEQ ID NO: 8:

```
GACAGAGGAT GTGAAGCATA TGTGCTGCGG GTCGGAAGAT GG                42
```

( 2 ) INFORMATION FOR SEQ ID NO: 9:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: oligonucleotide 9

( x i ) SEQUENCE DESCRIPTION: SEQ ID NO: 9:

```
ACATCAACAT CCGGAAGACC GCCGCCGCCC GGTGAAGGCT CTTCATGA          48
```

( 2 ) INFORMATION FOR SEQ ID NO: 10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: oligonucleotide 10

( x i ) SEQUENCE DESCRIPTION: SEQ ID NO: 10:

```
GGACTAGTGT CGACCCTGTC CATCCTGAAA GAGTTG                       36
```

( 2 ) INFORMATION FOR SEQ ID NO: 11:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: oligonucleotide 11

( x i ) SEQUENCE DESCRIPTION: SEQ ID NO: 11:

```
ACATCAACAT CCGGAAGACC GCCGCCGCCC GGCTTTGAAG GCTCTTCA                48
```

( 2 ) INFORMATION FOR SEQ ID NO: 12:

( i ) SEQUENCE CHARACTERISTICS:
        ( A ) LENGTH: 105 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: oligonucleotide 12

( x i ) SEQUENCE DESCRIPTION: SEQ ID NO: 12:

```
TTCGATGTCA GCCTGGACGG CGAGACCGCC ACGTTCCAGG ATTGGATCGG GGGCAACTAC    60
GTGAACATCC GCCGCACATC CAAGGCATGA AGGCTCTTCA TGACG                   105
```

( 2 ) INFORMATION FOR SEQ ID NO: 13:

( i ) SEQUENCE CHARACTERISTICS:
        ( A ) LENGTH: 102 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( C ) INDIVIDUAL ISOLATE: oligonucleotide 13

( x i ) SEQUENCE DESCRIPTION: SEQ ID NO: 13:

```
GATGTCAGCC TGGACGGCGA GACCGCCACG TTCCAGGATT GGATCGGGGG CAACTACGTG    60
AACATCCGCC GCACATCCAA GCTATGAAGG CTCTTCATGA CG                      102
```

( 2 ) INFORMATION FOR SEQ ID NO: 14:

( i ) SEQUENCE CHARACTERISTICS:
        ( A ) LENGTH: 939 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
  ( A ) ORGANISM: Nocardia lactamdurans
  ( C ) INDIVIDUAL ISOLATE: ATCC 27382

( i x ) FEATURE:
  ( A ) NAME/KEY: CDS
  ( B ) LOCATION: 1..939
  ( D ) OTHER INFORMATION: /gene= "cefE"

( x i ) SEQUENCE DESCRIPTION: SEQ ID NO: 14:

```
ATG ACG GAC GCG ACC GTG CCG ACC TTC GAT CTG GCC GAG CTG CGT GAG         48
Met Thr Asp Ala Thr Val Pro Thr Phe Asp Leu Ala Glu Leu Arg Glu
 1               5                  10                  15

GGC TTG CAC CAG GAG GAG TTC CGC CAC TGC CTG CGC GAG AAG GGC GTG         96
Gly Leu His Gln Glu Glu Phe Arg His Cys Leu Arg Glu Lys Gly Val
            20                  25                  30

TTC TAC CTC AAG GGC ACC GGG CTC GCC GAG GCG GAC CAC GCC TCG GCG        144
Phe Tyr Leu Lys Gly Thr Gly Leu Ala Glu Ala Asp His Ala Ser Ala
        35                  40                  45

CGG GAG ATC GCG GTG GAC TTC TTC GAC CAC GGC ACC GAG GCC GAG AAG        192
Arg Glu Ile Ala Val Asp Phe Phe Asp His Gly Thr Glu Ala Glu Lys
    50                  55                  60

AAG GCG GTG ATG ACG CCG ATC CCG ACC ATC CGG CGC GGG TAC GCC GGG        240
Lys Ala Val Met Thr Pro Ile Pro Thr Ile Arg Arg Gly Tyr Ala Gly
65                  70                  75                  80

CTG GAG TCC GAG AGC ACC GCG CAG ATC ACG AAC ACC GGC AAG TAC ACC        288
Leu Glu Ser Glu Ser Thr Ala Gln Ile Thr Asn Thr Gly Lys Tyr Thr
                85                  90                  95

GAC TAC TCG ATG TCG TAC TCG ATG GGC ACC GCG GAC AAC CTG TTC CCC        336
Asp Tyr Ser Met Ser Tyr Ser Met Gly Thr Ala Asp Asn Leu Phe Pro
            100                 105                 110

AGC GCC GAG TTC GAG AAG GCG TGG GAG GAC TAC TTC GCG CGG ATG TAC        384
Ser Ala Glu Phe Glu Lys Ala Trp Glu Asp Tyr Phe Ala Arg Met Tyr
        115                 120                 125

CGC GCT TCG CAG GAC GTC GCG CGG CAG GTG CTG ACC TCG GTC GGC GCG        432
Arg Ala Ser Gln Asp Val Ala Arg Gln Val Leu Thr Ser Val Gly Ala
    130                 135                 140

GAA CCC GAG GTC GGC ATG GAC GCC TTC CTC GAC TGC GAA CCC CTG CTG        480
Glu Pro Glu Val Gly Met Asp Ala Phe Leu Asp Cys Glu Pro Leu Leu
145                 150                 155                 160

CGC CTG CGC TAC TTC CCC GAG GTG CCC GAG GAT CGC GTG GCC GAG GAG        528
Arg Leu Arg Tyr Phe Pro Glu Val Pro Glu Asp Arg Val Ala Glu Glu
                165                 170                 175

CAG CCG CTG CGG ATG GCC CCG CAC TAC GAC CTC TCG ATC GTC ACC CTG        576
Gln Pro Leu Arg Met Ala Pro His Tyr Asp Leu Ser Ile Val Thr Leu
            180                 185                 190

ATC CAC CAG ACC CCT TGC GCG AAC GGG TTC GTC AGC CTG CAG GTC GAG        624
Ile His Gln Thr Pro Cys Ala Asn Gly Phe Val Ser Leu Gln Val Glu
        195                 200                 205

GTG GAC GGG TCC TAT GTG GAC ATC CCG GCG CAG CCG GGC GCG GTG CTG        672
Val Asp Gly Ser Tyr Val Asp Ile Pro Ala Gln Pro Gly Ala Val Leu
    210                 215                 220

GTG TTC TGC GGC GCG GTG GCG ACG CTG GTG GCC GAC GGC GCG ATC AAG        720
Val Phe Cys Gly Ala Val Ala Thr Leu Val Ala Asp Gly Ala Ile Lys
225                 230                 235                 240

GCG CCC AAG CAC CAC GTG GCC GCG CCC GGC GCG GAC AAG CGG GTG GGC        768
Ala Pro Lys His His Val Ala Ala Pro Gly Ala Asp Lys Arg Val Gly
                245                 250                 255

AGC AGC CGC ACC TCC AGC GTG TTC TTC CTG CGC CCC AAC GGG GAC TTC        816
Ser Ser Arg Thr Ser Ser Val Phe Phe Leu Arg Pro Asn Gly Asp Phe
            260                 265                 270

CGC TTC TCG GTG CCG CGG GCC AGG GAG TGC GGG TTC GAC GTC AGC ATC        864
```

| | | | | | | | | | | | | | | |
|---|---|---|---|---|---|---|---|---|---|---|---|---|---|---|
| Arg | Phe | Ser<br>275 | Val | Pro | Arg | Ala | Arg<br>280 | Glu | Cys | Gly | Phe | Asp<br>285 | Val | Ser | Ile |

| | | | | | | | | | | | | | | |
|---|---|---|---|---|---|---|---|---|---|---|---|---|---|---|
| CCG | GCC | GAG | ACC | GCC | ACC | TTC | GAC | GAC | TGG | ATC | GGC | GGC | AAC | TAC | ATC |
| Pro | Ala | Glu | Thr | Ala | Thr | Phe | Asp | Asp | Trp | Ile | Gly | Gly | Asn | Tyr | Ile |
| | 290 | | | | | 295 | | | | | 300 | | | | |

912

| | | | | | | | |
|---|---|---|---|---|---|---|---|
| AAC | ATC | CGG | AAG | ACC | GCC | GCC | CGG |
| Asn | Ile | Arg | Lys | Thr | Ala | Ala | Arg |
| 305 | | | | | 310 | | |

939

(2) INFORMATION FOR SEQ ID NO: 15:

(i) SEQUENCE CHARACTERISTICS:
        (A) LENGTH: 313 amino acids
        (B) TYPE: amino acid
        (D) TOPOLOGY: linear (ii) MOLECULE TYPE: protein (xi) SEQUENCE DESCRIPTION: SEQ ID NO: 15:

| | | | | | | | | | | | | | | |
|---|---|---|---|---|---|---|---|---|---|---|---|---|---|---|
| Met<br>1 | Thr | Asp | Ala | Thr<br>5 | Val | Pro | Thr | Phe | Asp<br>10 | Leu | Ala | Glu | Leu | Arg<br>15 | Glu |
| Gly | Leu | His<br>20 | Gln | Glu | Glu | Phe | Arg<br>25 | His | Cys | Leu | Arg | Glu<br>30 | Lys | Gly | Val |
| Phe | Tyr | Leu<br>35 | Lys | Gly | Thr | Gly | Leu<br>40 | Ala | Glu | Ala | Asp | His<br>45 | Ala | Ser | Ala |
| Arg | Glu<br>50 | Ile | Ala | Val | Asp | Phe<br>55 | Phe | Asp | His | Gly | Thr<br>60 | Glu | Ala | Glu | Lys |
| Lys<br>65 | Ala | Val | Met | Thr | Pro<br>70 | Ile | Pro | Thr | Ile | Arg<br>75 | Arg | Gly | Tyr | Ala | Gly<br>80 |
| Leu | Glu | Ser | Glu | Ser<br>85 | Thr | Ala | Gln | Ile | Thr<br>90 | Asn | Thr | Gly | Lys | Tyr<br>95 | Thr |
| Asp | Tyr | Ser | Met<br>100 | Ser | Tyr | Ser | Met | Gly<br>105 | Thr | Ala | Asp | Asn | Leu<br>110 | Phe | Pro |
| Ser | Ala | Glu<br>115 | Phe | Glu | Lys | Ala | Trp<br>120 | Glu | Asp | Tyr | Phe | Ala<br>125 | Arg | Met | Tyr |
| Arg | Ala<br>130 | Ser | Gln | Asp | Val | Ala<br>135 | Arg | Gln | Val | Leu | Thr<br>140 | Ser | Val | Gly | Ala |
| Glu<br>145 | Pro | Glu | Val | Gly | Met<br>150 | Asp | Ala | Phe | Leu | Asp<br>155 | Cys | Glu | Pro | Leu | Leu<br>160 |
| Arg | Leu | Arg | Tyr | Phe<br>165 | Pro | Glu | Val | Pro | Glu<br>170 | Asp | Arg | Val | Ala | Glu<br>175 | Glu |
| Gln | Pro | Leu | Arg<br>180 | Met | Ala | Pro | His | Tyr<br>185 | Asp | Leu | Ser | Ile | Val<br>190 | Thr | Leu |
| Ile | His | Gln<br>195 | Thr | Pro | Cys | Ala | Asn<br>200 | Gly | Phe | Val | Ser | Leu<br>205 | Gln | Val | Glu |
| Val | Asp<br>210 | Gly | Ser | Tyr | Val | Asp<br>215 | Ile | Pro | Ala | Gln | Pro<br>220 | Gly | Ala | Val | Leu |
| Val<br>225 | Phe | Cys | Gly | Ala | Val<br>230 | Ala | Thr | Leu | Val | Ala<br>235 | Asp | Gly | Ala | Ile | Lys<br>240 |
| Ala | Pro | Lys | His | His<br>245 | Val | Ala | Ala | Pro | Gly<br>250 | Ala | Asp | Lys | Arg | Val<br>255 | Gly |
| Ser | Ser | Arg | Thr<br>260 | Ser | Ser | Val | Phe | Phe<br>265 | Leu | Arg | Pro | Asn | Gly<br>270 | Asp | Phe |
| Arg | Phe | Ser<br>275 | Val | Pro | Arg | Ala | Arg<br>280 | Glu | Cys | Gly | Phe | Asp<br>285 | Val | Ser | Ile |
| Pro | Ala<br>290 | Glu | Thr | Ala | Thr | Phe<br>295 | Asp | Asp | Trp | Ile | Gly<br>300 | Gly | Asn | Tyr | Ile |

Asn Ile Arg Lys Thr Ala Ala Ala Arg
305                 310

( 2 ) INFORMATION FOR SEQ ID NO: 16:

( i ) SEQUENCE CHARACTERISTICS:
        ( A ) LENGTH: 942 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Nocardia lactamdurans
        ( C ) INDIVIDUAL ISOLATE: LC 411

( i x ) FEATURE:
        ( A ) NAME/KEY: CDS
        ( B ) LOCATION: 1..942
        ( D ) OTHER INFORMATION: /gene= "cefE"
            / citation= ([1])

( x ) PUBLICATION INFORMATION:
        ( A ) AUTHORS: Coque, J J
            Martin, J F
            Liras, P
        ( B ) TITLE: Characterization and expression in
            Streptomyces lividans of cefD and cefE genes from
            Nocardia lactamdurans: the organization of the
            cephamycin gene cluster differs from that in
            Streptomyces clavuligerus
        ( C ) JOURNAL: Mol. Gen. Genet.
        ( D ) VOLUME: 236
        ( F ) PAGES: 453-458
        ( G ) DATE: 1993

( x i ) SEQUENCE DESCRIPTION: SEQ ID NO: 16:

```
ATG ACG GAC GCG ACC GTG CCG ACC TTC GAT CTG GCC GAG CTG CGT GAG      48
Met Thr Asp Ala Thr Val Pro Thr Phe Asp Leu Ala Glu Leu Arg Glu
 1               5                  10                  15

GGC TTG CAC CAG GAG GAG TTC CGC CAC TGC CTG CGC GAG AAG GGC GTG      96
Gly Leu His Gln Glu Glu Phe Arg His Cys Leu Arg Glu Lys Gly Val
             20                  25                  30

TTC TAC CTC AAG GGC ACC GGG CTG CCG GCC GAG GCG GAC CAC GCC TCG     144
Phe Tyr Leu Lys Gly Thr Gly Leu Pro Ala Glu Ala Asp His Ala Ser
         35                  40                  45

GGC CGG GAG ATC GCG GTG GAC TTC TTC GAC CAC GGC ACC GAG GCC GAG     192
Gly Arg Glu Ile Ala Val Asp Phe Phe Asp His Gly Thr Glu Ala Glu
     50                  55                  60

AAG AAG GCG GTG ATG ACG CCG ATC CCG ACC ATC CGG CGC GGG TAC GCC     240
Lys Lys Ala Val Met Thr Pro Ile Pro Thr Ile Arg Arg Gly Tyr Ala
 65                  70                  75                  80

GGG CTG GAG TCC GAG AGC ACC GCG CAG ATC ACG AAC ACC GGC AAG TAC     288
Gly Leu Glu Ser Glu Ser Thr Ala Gln Ile Thr Asn Thr Gly Lys Tyr
                 85                  90                  95

ACC GAC TAC TCG ATG TCG TAC TCG ATG GGC ACC GCG GAC AAC CTG TTC     336
Thr Asp Tyr Ser Met Ser Tyr Ser Met Gly Thr Ala Asp Asn Leu Phe
             100                 105                 110

CCC AGC GCC GAG TTC GAG AAG GCG TGG GAG GAC TAC TTC GCG CGG ATG     384
Pro Ser Ala Glu Phe Glu Lys Ala Trp Glu Asp Tyr Phe Ala Arg Met
         115                 120                 125

TAC CGC GCT TCG CAG GAC GTC GCG CGG CAG GTG CTG ACC TCG GTC GGC     432
Tyr Arg Ala Ser Gln Asp Val Ala Arg Gln Val Leu Thr Ser Val Gly
     130                 135                 140
```

-continued

```
GCG GAA CCC GAG GTC GGC ATG GAC GCC TTC CTC GAC TGC GAA CCC CTG      480
Ala Glu Pro Glu Val Gly Met Asp Ala Phe Leu Asp Cys Glu Pro Leu
145                 150                 155                 160

CTG CGC CTG CGC TAC TTC CCC GAG GTG CCC GAG GAT CGC GTG GCC GAG      528
Leu Arg Leu Arg Tyr Phe Pro Glu Val Pro Glu Asp Arg Val Ala Glu
                    165                 170                 175

GAG CAG CCG CTG CGG ATG GCC CCG CAC TAC GAC CTC TCG ATC GTC ACC      576
Glu Gln Pro Leu Arg Met Ala Pro His Tyr Asp Leu Ser Ile Val Thr
            180                 185                 190

CTG ATC CAC CAG ACC CCT TGC GCG AAC GGG TTC GTC AGC CTG CAG GTC      624
Leu Ile His Gln Thr Pro Cys Ala Asn Gly Phe Val Ser Leu Gln Val
        195                 200                 205

GAG GTG GAC GGG TCC TAT GTG GAC ATC CCG GCG CAG CCG GGC GCG GTG      672
Glu Val Asp Gly Ser Tyr Val Asp Ile Pro Ala Gln Pro Gly Ala Val
210                 215                 220

CTG GTG TTC TGC GGC GCG GTG GCG ACG CTG GTG GCC GAC GGC GCG ATC      720
Leu Val Phe Cys Gly Ala Val Ala Thr Leu Val Ala Asp Gly Ala Ile
225                 230                 235                 240

AAG GCG CCC AAG CAC CAC GTG GCC GCG CCC GGC GCG GAC AAG CGG GTG      768
Lys Ala Pro Lys His His Val Ala Ala Pro Gly Ala Asp Lys Arg Val
                    245                 250                 255

GGC AGC AGC CGC ACC TCC AGC GTG TTC TTC CTG CGC CCC AAC GGG GAC      816
Gly Ser Ser Arg Thr Ser Ser Val Phe Phe Leu Arg Pro Asn Gly Asp
                260                 265                 270

TTC CGC TTC TCG GTG CCG CGG GCC AGG GAG TGC GGG TTC GAC GTC AGC      864
Phe Arg Phe Ser Val Pro Arg Ala Arg Glu Cys Gly Phe Asp Val Ser
            275                 280                 285

ATC CCG GCC GAG ACC GCC ACC TTC GAC GAC TGG ATC GGC GGC AAC TAC      912
Ile Pro Ala Glu Thr Ala Thr Phe Asp Asp Trp Ile Gly Gly Asn Tyr
        290                 295                 300

ATC AAC ATC CGG AAG ACC GCC GCC GCC CGG                              942
Ile Asn Ile Arg Lys Thr Ala Ala Ala Arg
305                 310
```

( 2 ) INFORMATION FOR SEQ ID NO: 17:

( i ) SEQUENCE CHARACTERISTICS:
        ( A ) LENGTH: 314 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 17:

```
Met Thr Asp Ala Thr Val Pro Thr Phe Asp Leu Ala Glu Leu Arg Glu
1               5                   10                  15

Gly Leu His Gln Glu Glu Phe Arg His Cys Leu Arg Glu Lys Gly Val
                20                  25                  30

Phe Tyr Leu Lys Gly Thr Gly Leu Pro Ala Glu Ala Asp His Ala Ser
            35                  40                  45

Gly Arg Glu Ile Ala Val Asp Phe Phe Asp His Gly Thr Glu Ala Glu
        50                  55                  60

Lys Lys Ala Val Met Thr Pro Ile Pro Thr Ile Arg Arg Gly Tyr Ala
65                  70                  75                  80

Gly Leu Glu Ser Glu Ser Thr Ala Gln Ile Thr Asn Thr Gly Lys Tyr
                85                  90                  95

Thr Asp Tyr Ser Met Ser Tyr Ser Met Gly Thr Ala Asp Asn Leu Phe
            100                 105                 110

Pro Ser Ala Glu Phe Glu Lys Ala Trp Glu Asp Tyr Phe Ala Arg Met
        115                 120                 125
```

| | | | | | | | | | | | | | | | |
|---|---|---|---|---|---|---|---|---|---|---|---|---|---|---|---|
| Tyr | Arg 130 | Ala | Ser | Gln | Asp | Val 135 | Ala | Arg | Gln | Val | Leu 140 | Thr | Ser | Val | Gly |
| Ala 145 | Glu | Pro | Glu | Val | Gly 150 | Met | Asp | Ala | Phe | Leu 155 | Asp | Cys | Glu | Pro | Leu 160 |
| Leu | Arg | Leu | Arg | Tyr 165 | Phe | Pro | Glu | Val | Pro 170 | Glu | Asp | Arg | Val | Ala 175 | Glu |
| Glu | Gln | Pro | Leu 180 | Arg | Met | Ala | Pro | His 185 | Tyr | Asp | Leu | Ser | Ile 190 | Val | Thr |
| Leu | Ile | His 195 | Gln | Thr | Pro | Cys | Ala 200 | Asn | Gly | Phe | Val | Ser 205 | Leu | Gln | Val |
| Glu | Val 210 | Asp | Gly | Ser | Tyr | Val 215 | Asp | Ile | Pro | Ala | Gln 220 | Pro | Gly | Ala | Val |
| Leu 225 | Val | Phe | Cys | Gly | Ala 230 | Val | Ala | Thr | Leu | Val 235 | Ala | Asp | Gly | Ala | Ile 240 |
| Lys | Ala | Pro | Lys | His 245 | His | Val | Ala | Ala | Pro 250 | Gly | Ala | Asp | Lys | Arg 255 | Val |
| Gly | Ser | Ser | Arg 260 | Thr | Ser | Ser | Val | Phe 265 | Phe | Leu | Arg | Pro | Asn 270 | Gly | Asp |
| Phe | Arg | Phe 275 | Ser | Val | Pro | Arg | Ala 280 | Arg | Glu | Cys | Gly | Phe 285 | Asp | Val | Ser |
| Ile | Pro 290 | Ala | Glu | Thr | Ala | Thr 295 | Phe | Asp | Asp | Trp | Ile 300 | Gly | Gly | Asn | Tyr |
| Ile 305 | Asn | Ile | Arg | Lys | Thr 310 | Ala | Ala | Ala | Arg | | | | | | |

PROCESS FOR THE EFFICIENT PRODUCTION OF 7-ADCA VIA 2-(CARBOXYETHYLTHIO)ACETYL-7-ADCA AND 3-(CARBOXYMETHYLTHIO) PROPIONYL-7-ADCA

FIELD OF THE INVENTION AND BRIEF DESCRIPTION OF THE PRIOR ART

The present invention concerns a biosynthetic process for preparation and recovery of 7-aminodesacetoxycephalosporanic acid (7-ADCA).

β-Lactam antibiotics constitute the most important group of antibiotic compounds, with a long history of clinical use. Among this group, the prominent ones are the penicillins and cephalosporins. These compounds are naturally produced by the filamentous fungi *Penicillium chrysogenum* and *Acremonium chrysogenum*, respectively.

As a result of classical strain improvement techniques, the production levels of the antibiotics in *Penicillium chrysogenum* and *Acremonium chrysogenum* have increased dramatically over the past decades. With the increasing knowledge of the biosynthetic pathways leading to penicillins and cephalosporins, and the advent of recombinant DNA technology, new tools for the improvement of production strains and for the in vivo derivatization of the compounds have become available.

Most enzymes involved in β-lactam biosynthesis have been identified and their corresponding genes been cloned, as can be found in Ingolia and Queener, Med. Res. Rev. 9 (1989), 245–264 (biosynthesis route and enzymes), and Aharonowitz, Cohen, and Martin, Ann. Rev. Microbiol. 46 (1992), 461–495 (gene cloning).

The first two steps in the biosynthesis of penicillin in *P. chrysogenum* are the condensation of the three amino acids L-5-amino-5-carboxypentanoic acid (L-α-aminoadipic acid) (A), L-cysteine (C) and L-valine (V) into the tripeptide LLD-ACV, followed by cyclization of this tripeptide to form isopenicillin N. This compound contains the typical β-lactam structure.

The third step involves the exchange of the hydrophilic side chain of L-5-amino-5-carboxypentanoic acid by a hydrophobic side chain by the action of the enzyme acyltransferase (AT). In the industrial process for penicillin production the side chain of choice is phenylacetic acid (PA). In EP-A-0532341 the application of an adipate (5-carboxypentanoate) feedstock has been disclosed. The incorporation of this substrate leads to a penicillin derivative with a 5-carboxypentanoyl side chain, viz. 5-carboxypentanoyl-6-aminopenicillanic acid. This incorporation is due to the fact that the acyltransferase has a proven wide substrate specificity (Behrens et al., J. Biol. Chem. 175 (1948), 751–809; Cole, Process. Biochem. 1 (1966), 334–338; Ballio et al., Nature 185 (1960), 97–99). The enzymatic exchange reaction mediated by AT takes place inside a cellular organelle, the microbody, as has been described in EP-A-0448180.

Cephalosporins are much more expensive than penicillins. One reason is that some cephalosporins (e.g. cephalexin) are made from penicillins by a number of chemical conversions. Another reason is that, so far, only cephalosporins with a D-5-amino-5-carboxypentanoyl side chain can be fermented. Cephalosporin C, by far the most important starting material in this respect, is very soluble in water at any pH, thus implying lengthy and costly isolation processes using cumbersome and expensive column technology. Cephalosporin C obtained in this way has to be converted into therapeutically used cephalosporins by a number of chemical and enzymetic conversions.

The intermediate 7-ADCA is currently produced by chemical derivatization of penicillin G. The necessary chemical steps to produce 7-ADCA involve the expansion of the 5-membered penicillin ring structure to a 6-membered cephalosporin ring structure. However, the expandase enzyme from the filamentous bacterium *Streptomyces clavuligerus* can carry out such ring expansions. When introduced into *P. chrysogenum*, it can convert the penicillin ring structure into the cephalosporin ring structure, as described in Cantwell et al., Proc. R. Soco Lond. B. 248 (1992), 283–289; and in EP-A-0532341 and EP-A-0540210. The expandase enzyme has been well characterized (EP-A-0366354) both biochemically and functionally, as has its corresponding gene. Both physical maps of the cefE gene (EP-A-0233715), DNA sequence and transformation studies in *P. chrysogenum* with cefE have been described.

Another source for a suitable ring expansion enzyme is the filamentous bacterium *Nocardia lactamdurans* (formerly *Streptomyces lactamdurans*). Both the biochemical properties of the enzyme and the DNA sequence of the gene have been described (Cortés et al., J. Gert. Microbiol. 133 (1987), 3165–3174; and Coque et al., Mol. Gen. Genet. 236 (1993), 453–458, respectively).

More particularly, EP-A-0532341 teaches the in vivo use of the expandase enzyme in *P. chrysogenum*, in combination with a 5-carboxypentanoyl side chain as a feedstock, which is used as a substrate for the acyltransferase enzyme in *P. chrysogenum*. This leads to the formation of 5-carboxypentanoyl-6-APA, which is converted by an expandase enzyme introduced into the *P. chrysogenum* strain to yield 5-carboxypentanoyl-7-ADCA. Finally, the removal of the 5-carboxypentanoyl side chain is suggested, yielding 7-ADCA as a final product. The patent application EP-A-0540210 describes a similar process for the preparation of 7-ACA, including the extra steps of converting the 3-methyl side chain of the ADCA ring into the 3-acetoxymethyl side chain of ACA. However, the aforesaid patent applications do not teach an efficient and economically effective process, because, first of all, the problem of timely expression of the expandase enzyme in the cell concomitant with the expression of the acyltransferase enzyme has not been recognized.

In contrast, the present invention provides an efficient process for producing 7-ADCA in which expandase and acyltransferase are expressed simultaneously.

In addition, the application of a new side chain precursor, viz. 3'-carboxymethylthiopropionic acid, is taught by the present invention. This precursor is very efficiently incorporated by *P. chrysogenum* into the corresponding penicillins, which are to be expanded by the subsequent action of the expandase enzyme.

Furthermore, until now no effective way has been described for recovering the 7-ADCA derivative from the fermentation broth before its deacylation. The present invention provides an effective solvent extraction procedure for the recovery of the 7-ADCA derivative.

By the present invention, a real efficient overall process is provided for the preparation of 7-ADCA, comprising reaction steps neither disclosed nor suggested in the prior art so far.

Also, by applying the present invention and analogous to the description given in EP-A-0540210, 7-ACA can be prepared in an efficient overall process in this way.

BRIEF DESCRIPTION OF THE FIGURES

FIG. 8A–B: DNA sequence of *Nocardia lactamdurans* cefE (Coque et al., supra), sequence ID No. 16, (lower lines) aligned with the DNA sequence of PCR product 1, sequence ID No. 14, (upper lines). Sequence listings ID No. 15 and ID No. 17 are the amino acid sequences derived from sequence ID No. 14 and No. 16, respectively

BRIEF DESCRIPTION OF THE SEQUENCE LISTING

Figure 1:
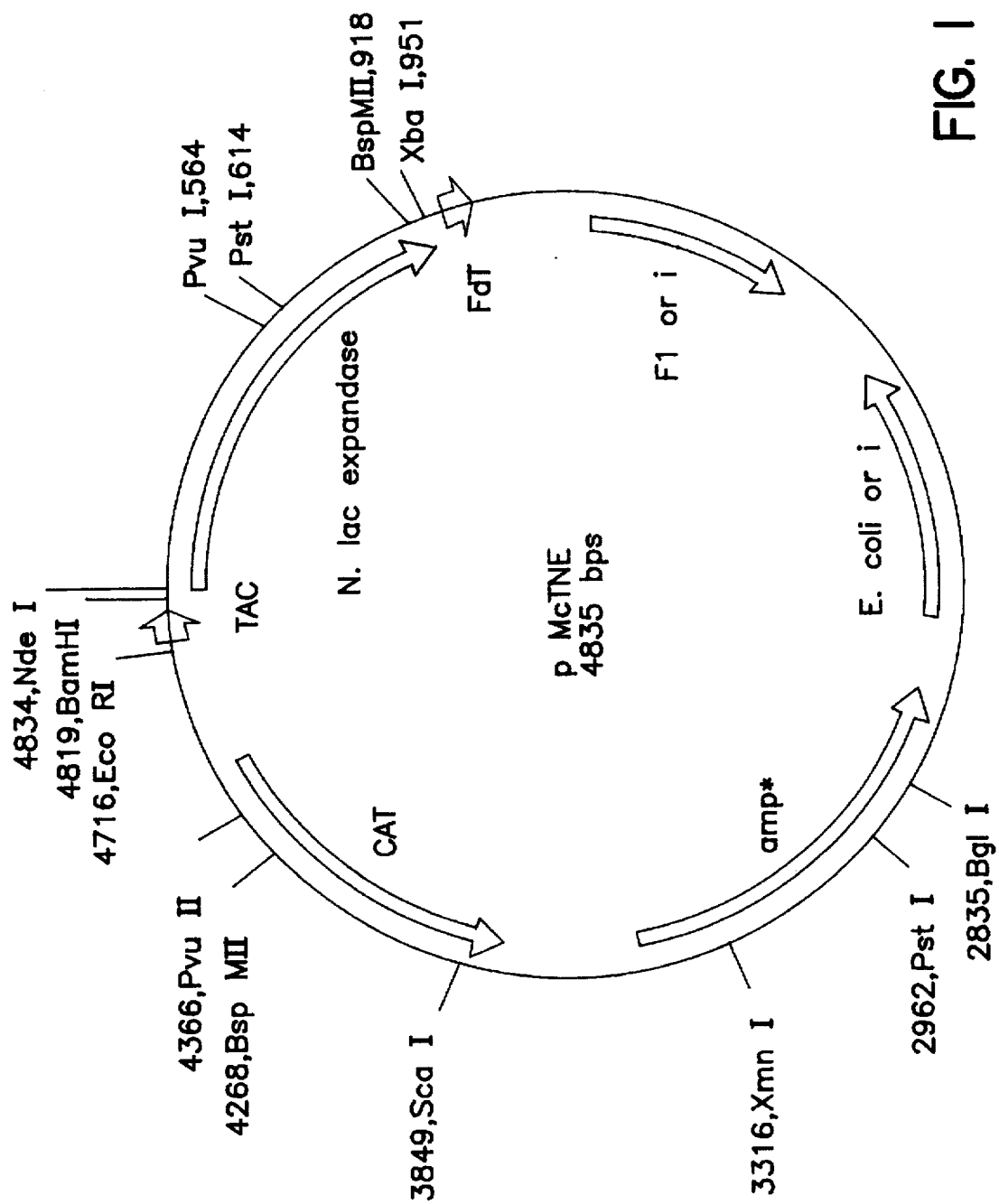
FIG. 1: A functional map of plasmid pMcTNE.

Sequence ID Nos. 1 to 13: oligonucleotides used in the construction of a *P. chrysogenum* expression cassette for the *Streotomyces clavuligerus* and *Nocardia lactamdurans* cefE genes.

Sequence ID No. 16: DNA sequence of *Nocardia lactamdurans* cefE (Coque et al., supra).

SUMMARY OF THE INVENTION

The present invention thus provides a process for the preparation and recovery of 7-aminodesacetoxycephalosporanic acid (7-ADCA) by:

a) transforming a *Penicillium chrysogenum* strain with an expandase gene, under the transcriptional and translational regulation of filamentous fungal expression signals;

b) fermenting said strain in a culture medium and adding to said culture medium 3'-carboxymethylthiopropionic acid or a salt or ester thereof suitable to yield 2-(carboxyethylthio)acetyl-and 3-(carboxymethylthio) propionyl-6-aminopenicillanic acid (2-(carboxyethylthio) acetyl- and 3-(carboxymethylthio)propionyl-6-APA), which are in situ expanded to form 2-(carboxyethylthio)-acetyl- and 3- (carboxymethylthio) propionyl-7-ADCA;

c) recovering the 2-(carboxyethylthio)acetyl- and 3-(carboxy-methylthio)propionyl-7-ADCA from the fermentation broth;

d) deacylating said 2-(carboxyethylthio)acetyl- and 3-(carboxymethylthio)propionyl-7-ADCA; and e) recovering the crystalline 7-ADCA.

Preferably, step (e) is a filtration step.

Preferably, the expression of the expandase gene is under the transcriptional and translational regulation of the respective control elements of the AT-gene, providing a simultaneous timing of expression of said genes.

Preferably, 2-(carboxyethylthio)acetyl- and 3-(carboxymethyl-thio)propionyl-7-ADCA are recovered from the fermentation broth by extracting the broth filtrate with an organic solvent immiscible with water at a pH of lower than about 4.5 and back-extracting the same with water at a pH between 4 and 10.

Moreover, a recombinant DNA vector comprising the DNA encoding expandase, functionally linked to the transcriptional and translational control elements of the AT-gene of *P. chrysogenum* or the *A. nidulans* gpda gene, and host cells transformed with the same, are provided.

DETAILED DESCRIPTION OF THE INVENTION

The present invention concerns the use of functional gene constructs in *P. chrysogenum* for the in vivo expansion of the penicillin ring structure, in combination with the use of a new substrate for the biosynthetic enzymes to form a derivative of a key intermediate in the cephalosporin biosynthesis, 7-amino-desacetoxycephalosporanic acid, or 7-ADCA. This derivative has a chemical composition so as to allow efficient solvent extraction, thus providing an economically attractive recovery process.

Transformation of *P. chrysogenum* can, in principle, be achieved by different means of DNA delivery, like PEG-Ca mediated protoplast uptake, electroporation or particle gun techniques, and selection of transformants. See for example Van den Hondel en Punt, Gene Transfer and Vector Development for Filamentous Fungi, in: Applied Molecular Genetics of Fungi (Peberdy, Laten, Ogden, Bennett, eds.), Cambridge University Press (1991). The application of dominant and non-dominant selection markers has been described (Van den Hondel, supra). Selection markers of both homologous (*P. chrysogenum* derived) and heterologous (non-*P. chrysogenum* derived) origin have been described.

The application of the different transformant selection markers, homologous or heterologous, in the presence or absence of vector sequences, physically linked or not to the non-selectable DNA, in the selection of transformants are well known.

Preferably a homologous selection marker is used to select transformants of *P. chrysogenum* to limit the amount of heterologous DNA introduced into *P. chrysogenum*. Most preferably a dominant selection marker is used which can be selectively removed from the transformed strain, e.g. the amdS gene of *A. nidulans* or other filamentous fungi (European patent application No. 94201896.1). These preferred characteristics of the *P. chrysogenum* transformant selection marker are very beneficial in process and product registration procedures since no antibiotic resistance markers are involved in the process or will be introduced into the environment.

The most preferred embodiment, the amdS selection marker which can be selectively removed from the strain, allows repeated rounds of transformation using the same dominant selection over and over again. This selection-marker free feature of the novel expandase expressing *P. chrysogenum* strains is crucial for the rapid development of high-producing strains in an industrial strain improvement programme.

The ring-expansion reaction, mediated by the expandase enzyme is introduced into and expressed in this way in *P. chrysogenum*, for instance in strain Wisconsin 54–1255. This ring-expansion reaction is also carried out in mutants thereof having an improved β-lactam yield. It will be clear that in that case, the medium conditions have to be slightly adapted to obtain an efficient growth.

Furthermore, the cefE gene is placed under the transcriptional and translational control of the respective filamentous fungel gene control elements, preferably derived from *P. chrysogenum* acyltransferase (AT) gene, thus allowing its expression in the optimal time frame, synchronized with the action of the acyltransferase enzyme itself. These measures are crucial for the effectiveness of the ring-expansion reaction on the penicillin molecule.

In addition to synchronised expression of the expandase and acyltransferase encoding genes, intracellular co-locatisation of part of the expandase enzymes with acyl-transferase in microbodies (the intracellular location of acyltransferase) might be advantageous for the development of an economical production process. These preferred embodiments will contribute enormously to reduce the amount of penicillin by-products, which are not tolerated in the 7-ADCA end product by registration authorities.

In summary, the present invention teaches how the activity of an expandase enzyme introduced into *P. chrysogenum* can be dedicated to the ring expansion of the penicillin ring in terms of synchronized expression.

In accordance with this invention β-lactam intermediates 2-(carboxyethylthio)acetyl- and 3-(carboxymethhylthio) propionyl-7-ADCA, are produced in *P. chrysogenum* by adding 3-carboxymethylthio propionic acid or a salt or ester thereof. Suitable salts are for instance those of sodium or potassium. The same are efficiently recovered from the media through a simple solvent extraction, for instance, as follows:

The broth is filtered and an organic solvent immiscible with water is added to the filtrate. The pH is adjusted in order to extract the cephalosporin from the aqueous layer. The pH range has to be lower than 4.5; preferably between 4 and 1, more preferably between 2 and 1.In this way the cephalosporin is separated from many other impurities present in the fermentation broth. Preferably a small volume of organic solvent is used, giving a concentrated solution of the cephalosporin, so achieving reduction of the volumetric flow rates. A second possibility is whole broth extraction at a pH of 4 or lower. Preferably the broth is extracted between 4 and 1 with an organic solvent immiscible with water.

Any solvent that does not interfere with the cephalosporin molecule can be used. Suitable solvents are, for instance, butyl acetate, ethyl acetate, methyl isobutyl ketone, alcohols like butanol etc. Preferably 1-butanol or isobutanol are used.

Hereafter the cephalosporin is back extracted with water at a pH between 4 and 10, preferably between 6 and 9. Again the final volume is reduced drastically. The recovery can be carried out at temperatures between 0° and 50° C., and preferably at ambient temperatures.

The aqueous cephalosporin solution thus obtained is treated with a suitable enzyme in order to remove the 2-(carboxyethylthio)-acetyl- and 3- (carboxymethylthio) propionyl side chain and obtain the desired 7-ADCA.

Preferably, an immobilized enzyme is used, in order to be able to use the enzyme repeatedly. The methodology for the preparation of such particles and the immobilization of the enzymes have been described extensively in EP-A-0222462. The pH of the aqueous solution has a value of, for example pH 4 to pH 9, at which the degradation reaction of cephalosporin is minimized and the desired conversion with the enzyme is optimized. Thus, the enzyme is added to the aqueous cephalosporin solution while maintaining the pH at the appropriate level by, for instance, adding an inorganic base, such as a potassium hydroxide solution, or applying a cation exchange resin. When the reaction is completed the immobilized enzyme is removed by filtration. Another possibility is the application of the immobilized enzyme in a fixed or fluidized bed column, or using the enzyme in solution and removing the products by membrane filtration. Subsequently, the reaction mixture is acidified in the presence of an organic solvent immiscible with water.

Suitable enzymes are, for instance, derived from a Pseudomonas SY77 microorganism having a mutation in one or more of the positions 62,177,178 and 179. Also enzymes from other Pseudomonas microorganisms, preferably Pseudomonas SE83, optionally having a mutation in one or more of the positions corresponding to the 62, 177, 178 and 179 positions in Pseudomonas SY77, may be used.

After adjusting the pH to about 0.1 to 1.5, the layers are separated and the pH of the aqueous layer is adjusted to 2 to 5. The crystalline 7-ADCA is then filtered off.

The deacylation can also be carried out chemically as known in the prior art, for instance, via the formation of an imino-chloride side chain, by adding phosphorus pentachloride at a temperature of lower than 10° C. and subsequently isobutanol at ambient temperatures or lower.

The following examples are offered by way of illustration and not by way of limitation.

EXAMPLES

Example 1

Expression of the Streptomyces and Nocardia cefE gene in *Penicillium chrysogenum* a. General gene cloning and gene transformation procedures

Common techniques used in gene cloning procedures are used in the present application. These techniques include polymerase chain reactions (PCR), synthetic oligonucleotide synthesis, nucleotide sequence analysis of DNA, enzymetic ligation and restriction of DNA, *E. coli* vector subcloning, transformation, and transformant selection, isolation and purification of DNA, DNA characterization by Southern blot analyses and $^{32}$p labelled probes, $^{32}$p labelling of DNA by random priming. These techniques are all very well known in the art and adequately described in many references. See for example Sambrook et al., Molecular Cloning, a Laboratory Manual, Cold Spring Harbor, U.S.A. (1989), Innes et al., PCR protocols, a Guide to Methods and Applications, Academic Press (1990), and McPherson et al., PCR, a Practical Approach, IRL Press (1991).

General procedures used in transformation of filamentous fungi and transformant selection include preparation of fungal protoplasts, DNA transfer and protoplast regeneration conditions, transformant purification and characterization. These procedures are all known in the art and very well documented in: Finkelstein and Ball (eds.), Biotechnology of Filamentous Fungi, technology and products, Butterworth-Heinemann (1992); Bennett and Lasure (eds.), More Gene Manipulations in Fungi, Academic Press (1991); Turner, in: Pühler (ed.), Biotechnology, second completely revised edition, VCH (1992).

More specific applications of gene cloning and gene transformation technology to *Penicillium chrysogenum* are very well documented in Bennett and Lasure (supra) and Finkelstein and Ball (supra).

Synthetic DNA oligonucleoides are synthesized, using a commercial DNA synthesizer (Applied Biosystems, CA, U.S.A.) according to the instructions of the manufacturer.

PCR is performed using a commercial automatic PCR apparatus (Perkin Elmer, U.S.A.) and Ultma DNA polymerase (Perkin Elmer) according to the instructions of the manufacturer.

The hGC PCR protocol (Dutton et al., Nucleic Acids Res. 21, (No. 12)(1993) 2953-2954) was used to be able to amplify the cefE coding regions of the *N. lactamdurans* and the *S. clavuligerus* chromosomal DNA.

Restriction enzymes and other DNA modification enzymes are from BRL (MD.,U.S.A.) and used according to the instructions of the manufacturer.

*E. coli* vector pBluescript® is obtained from Stratagone (CA, U.S.A.).

Other chemicals used are all analytical grade, obtained from various suppliers.

DNA nucleotide sequence analysis is performed using an automatic DNA sequence analysis apparatus (Applied Biosystems) based upon detection of sequence-specific fluorescent labelling according to the instructions of the manufacturer.

b. Culturing of microorganisms

*Streptomyces clavuligerus* ATCC 27064 is grown in tryptic soy broth (Difco). Chromosomal DNA of this strain is used for isolation of the cefE gene (Kovacevic et al., J. Bacteriol. (1989), 754–760).

*Nocardia lactamdurans* ATCC 27382 is also grown in tryptic soy broth (Difco). Chromosomal DNA of this strain is used for isolation of the cefE gene (Coque et al., supra).

*Penicillium chrysogenum* Wisconsin 54 . 1255 (ATCC 28089) is grown in complete YPD medium (YPD; 1% yeast extract, 2% peptone, 2% glucose). Chromosomal DNA of this strain is used for the isolation of penDE gene 5' and 3' regulatory regions required for cefE gene expression. *Penicillium chrysogenum* ATCC 28089 is also used as a host for cefE gene transformation experiments. Other strains of *Penicillium chrysogenum*, including mutants of strain Wisconsin 54–1255, having an improved β-lactam yield, are also suitable. Depending on the transformant selection marker used, *P. chrysogenum* strains containing mutations in the pyrG, niaD or facA gene may be used. These mutant strains can be obtained by methods well-known in the art (Cantoral, Bio/Technol. 5 (1987), 494–497; Gouka et al., J. Biotechn. 20 (1991), 189–200; and Gouka et al., Appl. Microbiol. Biotechnol. (1993), 514–519).

Culturing of *P. chrysogenum* for generation of protoplasts used in transformation is also done in YPD-medium.

It is well known in the art that the protoplasting and regeneration procedures may differ slightly depending on the particular strain of *Penicillium chrysogenum* used and the transformant selection procedure applied.

*E. coli* WK6 (Zell and Fritz, EMBO J. 6 (1987), 1809–1815), XL1-Blue (Stratagene) and HB101 (Boyer and Roulland-Dussoix, J. Mol. Biol., 41 (1969), 459; Bolivar and Backman, Messages Enzymol. 68 (1979), 2040) are maintained and cultured by using standard *E. coli* culture media (Sambrook, supra).

c. Construction of cefE expression cassettes

The cefE expression cassettes are listed in Table I, which also explains the nomenclature that has been used for these plasmids.

TABLE I

List of cefE expression cassettes that were constructed

Legends:
[1]tac = trp-lac hybrid promoter
[2]gpd = 5'-end of *A. nidulans* gpdA gene
[3]AT = 3'-end of *P. chrysogenum* penDE gene
[4]AT = 5'-end of *P. chrysogenum* penDE gene

| Plasmid | Promoter | Gene | Microbody targeting | Terminator |
|---------|----------|------|---------------------|------------|
| pMCTSE | tac[1] | S. cla cefE | | FdT |
| pMCTNE | tac | N. lac cefE | | Fdt |
| pGSE | gpd[2] | S. cla cefE | | — |
| pGNE | gpd | N. lac cefE | | — |
| pGNETA | gpd | N. lac cefE | + target | AT[3] |
| pGNEWA | gpd | N. lac cefE | Wt | AT |
| pANETA | AT[4] | N. lac cefE | + target | AT |
| pANEWA | AT | N. lac cefE | Wt | AT |
| pGSETA | gpd | S. cla cefE | + target | AT |
| pGSEWA | gpd | S. cla cefE | Wt | AT |
| pASETA | AT | S. cla cefE | + target | AT |
| pASEWA | AT | S. cla cefE | Wt | AT |

Published nucleotide sequences of the *S. clavuligerus* cefE gene (Kovacevic, supra); the *N. lactamdurans* cefE gene (Coque, supra); the *A. nidutans* gDdA gene (Punt et al., Gene 69 (1988) . 49–57); and the *P. chrysogenum* penDE gene (Barredo et al., Gene 83 (1989), 291–300; Diez et al., Mol. Gen. Genet. 218 (1989), 572–576) have been used to design synthetic oligonucleotides listed in Table II.

TABLE II

Oligonucleotides used in the construction of a *P. chrysogenum* expression cassettes for the *N. lactamdurans* and the *S. clavuligerus* cefE gene

| | |
|---|---|
| Sequence ID No. 1. | 5'-GCT GAA GGA GCT GAG CAT ATG ACG GAC GCG ACC GTG CCG ACC-3' |
| Sequence ID No. 2. | 5'-CCC GGG TCT AGA TCT AGA TCA CCG GGC GGC GGC GGT CTT CCG GAT GTT-3' |
| Sequence ID No. 3. | 5'-GAT CAG TGA GAG TTG CAT ATG GAC ACG ACG GTG CCC ACC TTC AGC CTG-3' |
| Sequence ID No. 4. | 5'-CCC GGG TCT AGA TCT AGA CTA TGC CTT GGA TGT GCG GCG GAT GTT-3' |
| Sequence ID No. 5. | 5'-GAG CTC TGT GAA TTC ACA GTG ACC GGT GAC TCT TTC-3' |
| Sequence ID No. 6. | 5'-GGG AGC CAT ATG GAT GTC TGC TCA AGC GGG GTA GCT-3' |
| Sequence ID No. 7. | 5'-AGA ACG GAT TAG TTA GTC TGA ATT CAA CAA GAA CGG CCA GAC-3' |
| Sequence ID No. 8. | 5'-GAC AGA GGA TGT GAA GCA TAT GTG CTG CGG GTC GGA AGA TGG-3' |
| Sequence ID No. 9. | 5'-ACA TCA ACA TCC GGA AGA CCG CCG CCG CCC GGT GAA GGC TCT TCA TGA-3' |
| Sequence ID No. 10 | 5'-GGA CTA GTG TCG ACC CTG TCC ATC CTG AAA GAG TTG-3' |
| Sequence ID No. 11 | 5'-ACA TCA ACA TCC GGA AGA CCG CCG CCG CCC GGC TTT GAA GGC TCT TCA-3' |
| Sequence ID No. 12 | 5'-TTC GAT GTC AGC CTG GAC GGC GAG ACC GCC ACG TTC CAG GAT TGG ATC GGG GGC AAC TAC GTG AAC ATC CGC CGC ACA TCC AAG GCA TGA AGG CTC TTC ATG ACG-3' |
| Sequence ID No. 13 | 5'-GAT GTC AGC CTG GAC GGC GAG ACC GCC ACG TTC CAG GAT TGG ATC GGG GGC AAC TAC GTG AAC ATC CGC CGC ACA TCC AAG CTA TGA AGG CTC TTC ATG ACG-3' | c1. Construction of the *E. coli* cefE expression plasmids pMCTSE and pMCTNE

PCR, 1: *N. lactamdurans* cefE

In a first PCR using chromosomal DNA of *N. lactamdurans* and oligonucleotides 1 and 2, the *N. lactamdurans* cefE open reading frame was obtained as a 0.9 kb PCR product, containing a unique NdeI restriction site at the 5'-end and a unique XbaI site at the 3'-end.

PCR, 2: *S. clavuligerus* cefE

In a second PCR using chromosomal DNA of *S. clavuligerus* and oligonucleotides 3 and 4, the *S. clavuligerus* cefE open reading frame was obtained as a 0.9 kb PCR product, also containing a unique NdeI restriction site at the 5'-end and a unique XbaI restriction site at the 3'-end.

Figure 3:
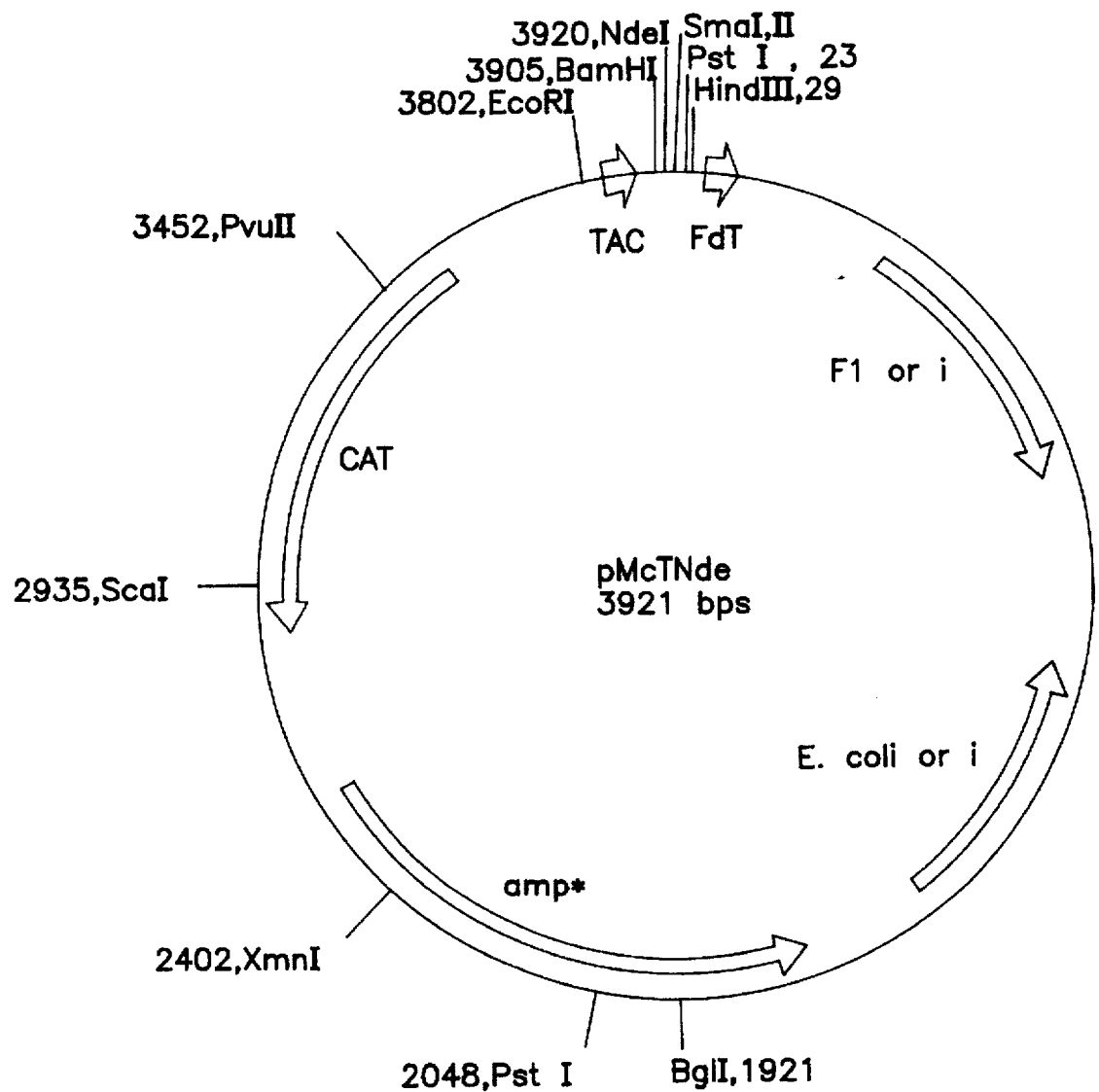
FIG. 3: A functional map of plasmid pMcTNde.

For the purpose of obtaining expression of the cefE genes in *E. coli* and characterisation of the PCR products by DNA sequence analysis, PCR products 1 and 2 were cloned in the lo vector pMCTNde, a derivative of pMC-5 (Stanssens et al., Nucleic Acids Res. 17 (1989), 4441). Plasmid pMCTNde was derived from pMC5-8 (European patent application No. 0351029) by insertion of a fragment encoding the tac promoter followed by a RBS site and a NdeI cloning site (FIG. 3).

PCR products 1 and 2 were digested with NdeI and XbaI and ligated into NdeI-XbaI digested vector pMCTNde. The ligation mixture was used to transform *E. coli* WK6. Transformants were selected for resistance to chloramphenicol.

These transformants are used to isolate plasmid DNA. The cefE expression cassette insert is first analyzed by restriction enzyme digestion on the predicted generation of restriction fragments. Plasmids containing the predicted restriction enzyme sites are finally analyzed by automated DNA sequence analysis.

Figure 2:
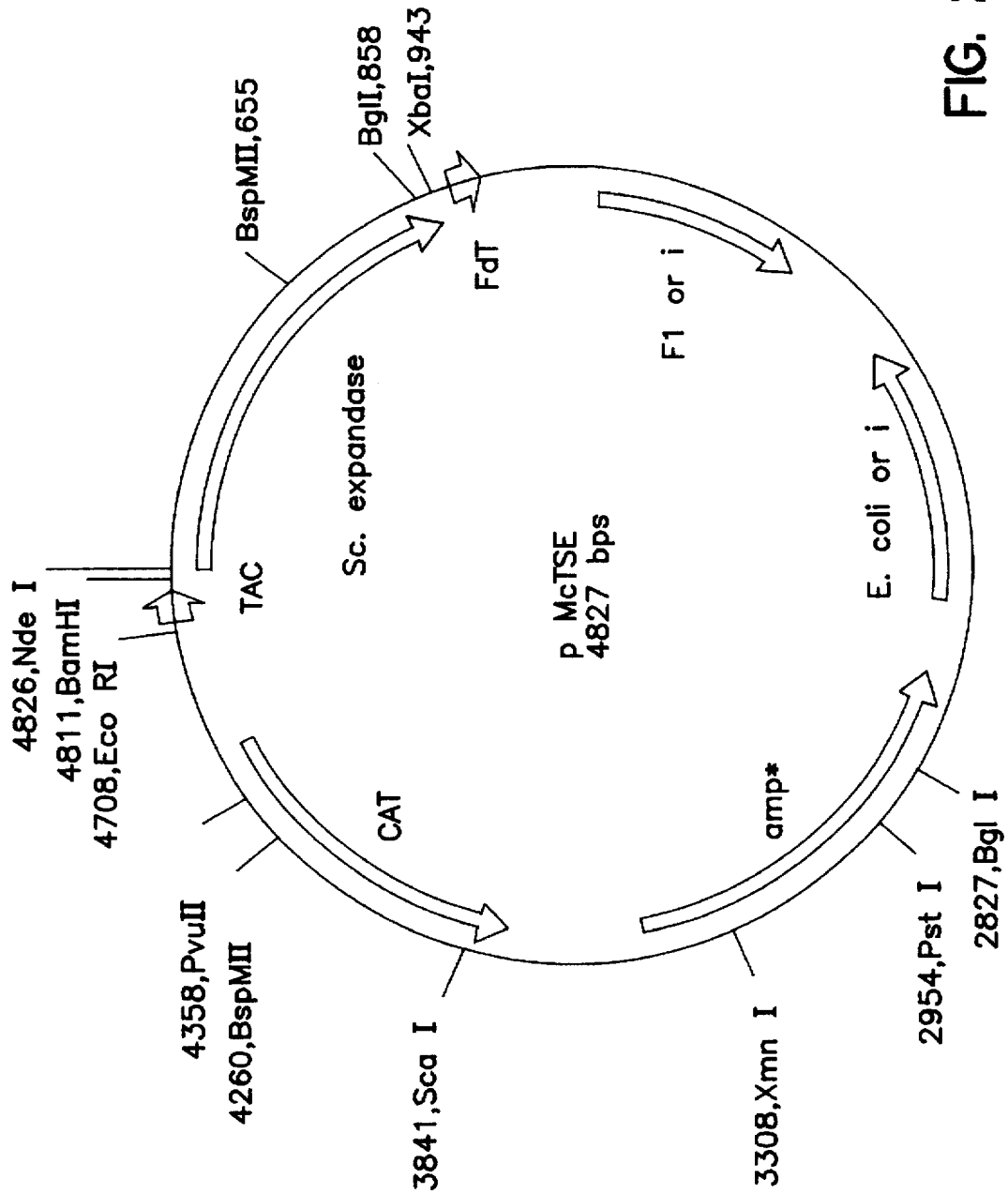
FIG. 2: A functional map of plasmid pMcTSE.

The DNA sequence of the *S. clavuligerus* cefE open reading frame in plasmid pMCTSE (FIG. 2) was 100% identical to the published sequence (Kovacevic, supra).

The DNA sequence (FIG. 8) of all the clones that were analyzed, containing the *N. lactamdurans* cefE open reading frame, was different from the published sequence (Coque, supra).

The derived amino acid sequence of the published *N. lactamdurans* cefE gene has a proline at amino acid position 41 (see Seq. ID No. 16). This proline is missing in the clones that were obtained in PCR 1. This plasmid is called pMCTNE (FIG. 1).

c2. Construction of the *P. chrysogenum* cefE expression plasmids

PCR, 3: gpdA promoter

In this third PCR, using pAN7-1 plasmid DNA (Punt et al., Gene 56 (1987), 117–124), containing the *E. coli* hDh gene under control of the *A. nidulans* gpdA promoter and oligonucleotides 5 and 6, the gpdA promoter was obtained as a 0.9 kb PCR product containing a unique EcoRI restriction site at the 5'-end and a unique NdeI site at the 3'-end.

PCR, 4: AT promoter

In the fourth PCR chromosomal DNA of *P. chrysogenum* and oligonucleotides 7 and 8 were used to obtain an AT promoter fragment of 1.5 kb, that also contains a unique EcoRI restriction site at the 5'-end and a unique NdeI site at the 3'-end.

PCR, 5: AT terminator and 3'-end of *N. lactamdurans* cefE gene

In a fifth PCR a 0.5 kb penDE (AT) terminator region was obtained using chromosomal DNA of *P. chrysogenum* and oligo-nucleotides 9 and 10, and 11 and 10, respectively. These PCR products thus contain the 3'-terminal sequence of the cefE gene with or without a microbody targeting signal, consisting of a C-terminal amino acid sequence ARL (M üller et al., Biochimica et Biophysica Acta 1116 (1992), 210–213).

The oligonucleotides are designed in such a way that a unique BspEI site is introduced at the 5'-end of the PCR product and a unique SpeI site is introduced at the 3'-end of the PCR product.

PCR, 6: AT terminator and 3.-end of *S. clavuligerus* cefE gene

In this sixth PCR the 0.5 kbpenDE (AT) terminator region was obtained using chromosomal DNA of *P. chrysogenum* and oligo-nucleotides 12 and 10, and 13 and 10, respectively. These PCR products thus contain the 3'-terminal sequence of the *S. clavuligerus* cefE gene with or without a microbody targeting signal, consisting of a C-terminal amino acid sequence SKL (De Hoop et al., Biochem. J. 286 (1992), 657–669).

The oligonucleoiides are designed in such a way that a unique BalI restriction site is introduced at the 5'-end of the PCR product and a unique speI site is obtained at the 3'-end of the PCR product.

For the purpose of obtaining expression of the cefE genes in *P. chrysogenum* the gpdA promoter and the AT promoter fragment were ligated to the cefE fragments from the plasmids pMCTNE and pMCTSE. These ligated fragments were cloned into the vector pBluescript II KS.

PCR 3 was digested with EcoRI and NdeI. pMCTNE and pMCTSE were digested with NdeI and XbaI. The restriction fragments were separated by agerose gel electrophoresis. The 0.9 kb cefE coding fragments were purified from the agerose gel. The EcoRI-NdeI promoter fragment was ligated together with the NdeI-XbaI cefE fragments into EcoRI-XbaI digested vector pBluescript II KS. Thus the following plasmids were obtained: pGSE and pGNE.

To obtain optimal expression of the cefE genes in *P. chrysogenum* we chose to clone the AT termination signal sequence behind the cefE genes in the Penicillium expression plasmids mentioned above.

pGNETA-pGNEWA

Figure 4:
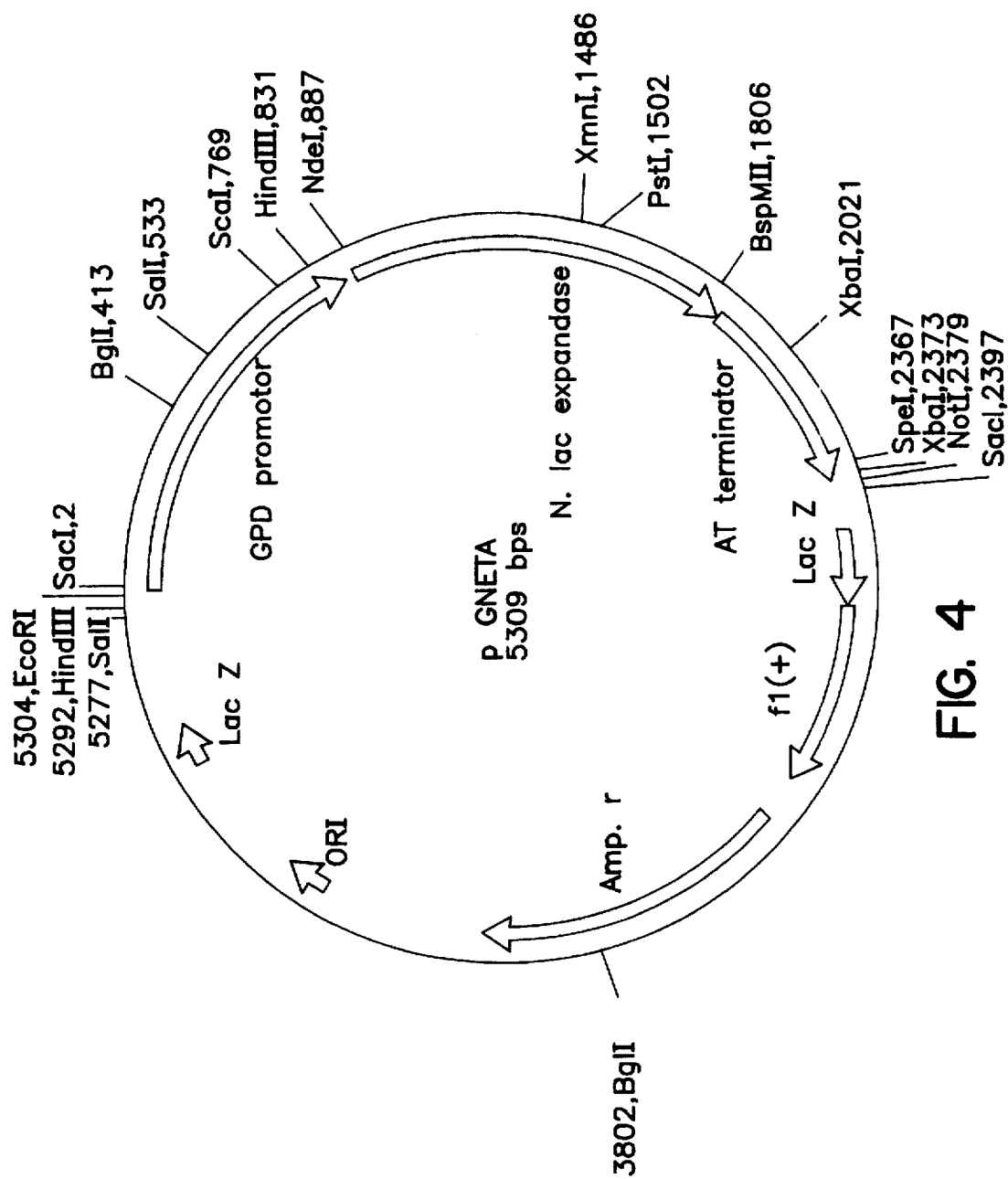
FIG. 4: A functional map of plasmid pGNETA.

PCR 5 products were digested with BspEI and SpeI and ligated into BspEI and SpeI digested vector pGNE. Ligation mixtures were used to transform *E. coli* HB101. Transformants were selected for resistance to ampicillin. Plasmids isolated from these transformants were characterized by restriction fragment analysis and later by DNA sequence analysis. Thus the following plasmids were obtained: pGNEWA and pGNETA (FIG. 4).

pGSETA-pGSEWA

Figure 5:
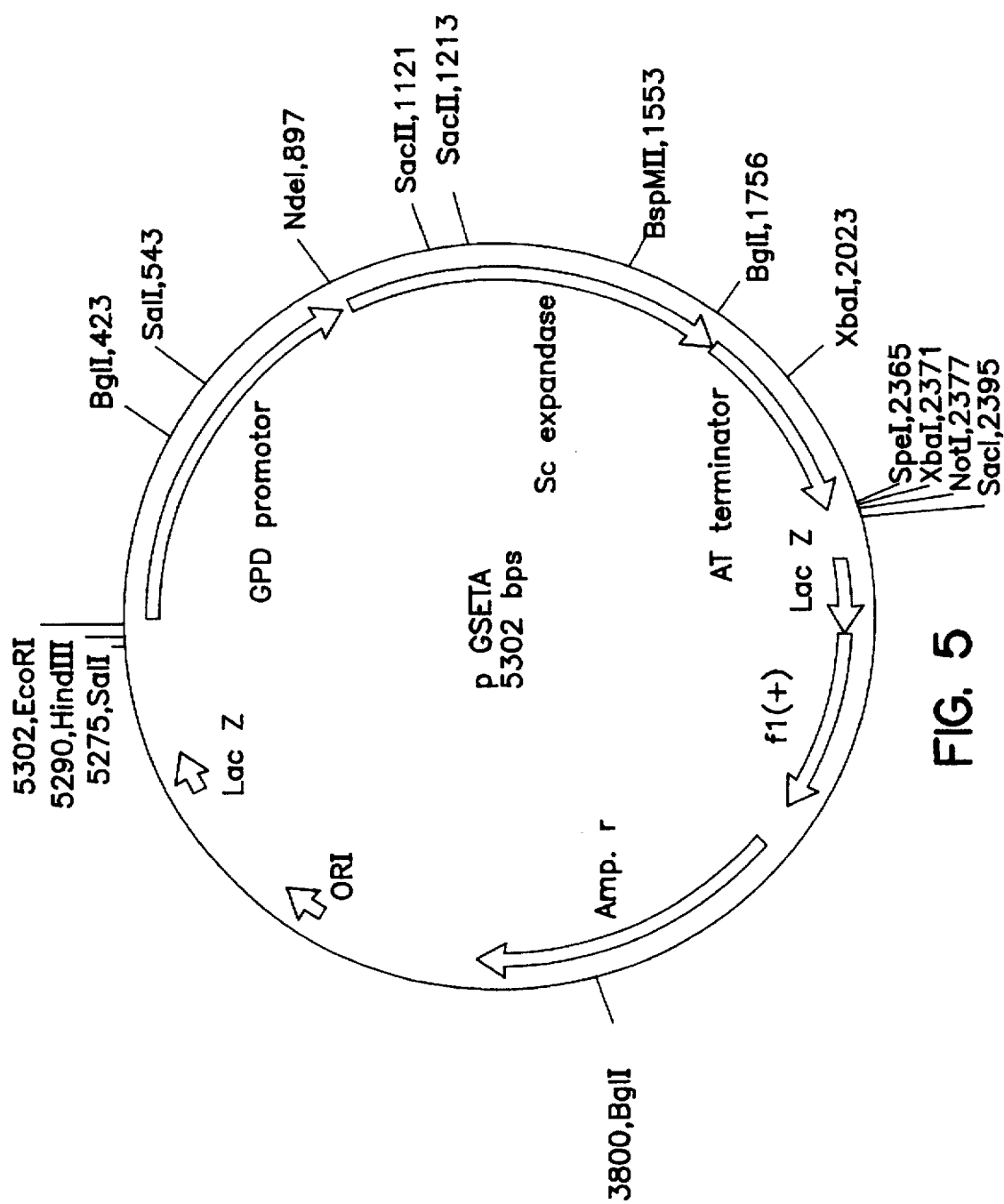
FIG. 5: A functional map of plasmid pGSETA.

PCR 6 products were digested with BglI and SpeI and ligated into BglI and SpeI digested vector pGSE. Ligation mixtures were used to transform *E. coli* HB101. Transformants were selected for resistance to ampicillin. Plasmids isolated from these transformants were also characterized by restriction fragment analysis and later by DNA sequence analysis. Thus the following plasmids were obtained: pGSEWA and pGSETA (FIG. 5).

pANETA, pANEWA and pASETA and pASEWA

The plasmids pGNETA, pGNEWA, pGSETA and pGSEWA were digested with EcoRI and NdeI. The restriction fragments were separated by agerose gel etectrophoresis and the 4.5 kb fragments were purified from the gel.

PCR 4 product was digested with EcoRI and NdeI and ligated with the purified fragments mentioned above. After transformation of the ligation mixtures into *E. coli* HB101, transformants were selected for ampicillin resistance.

Figure 6:
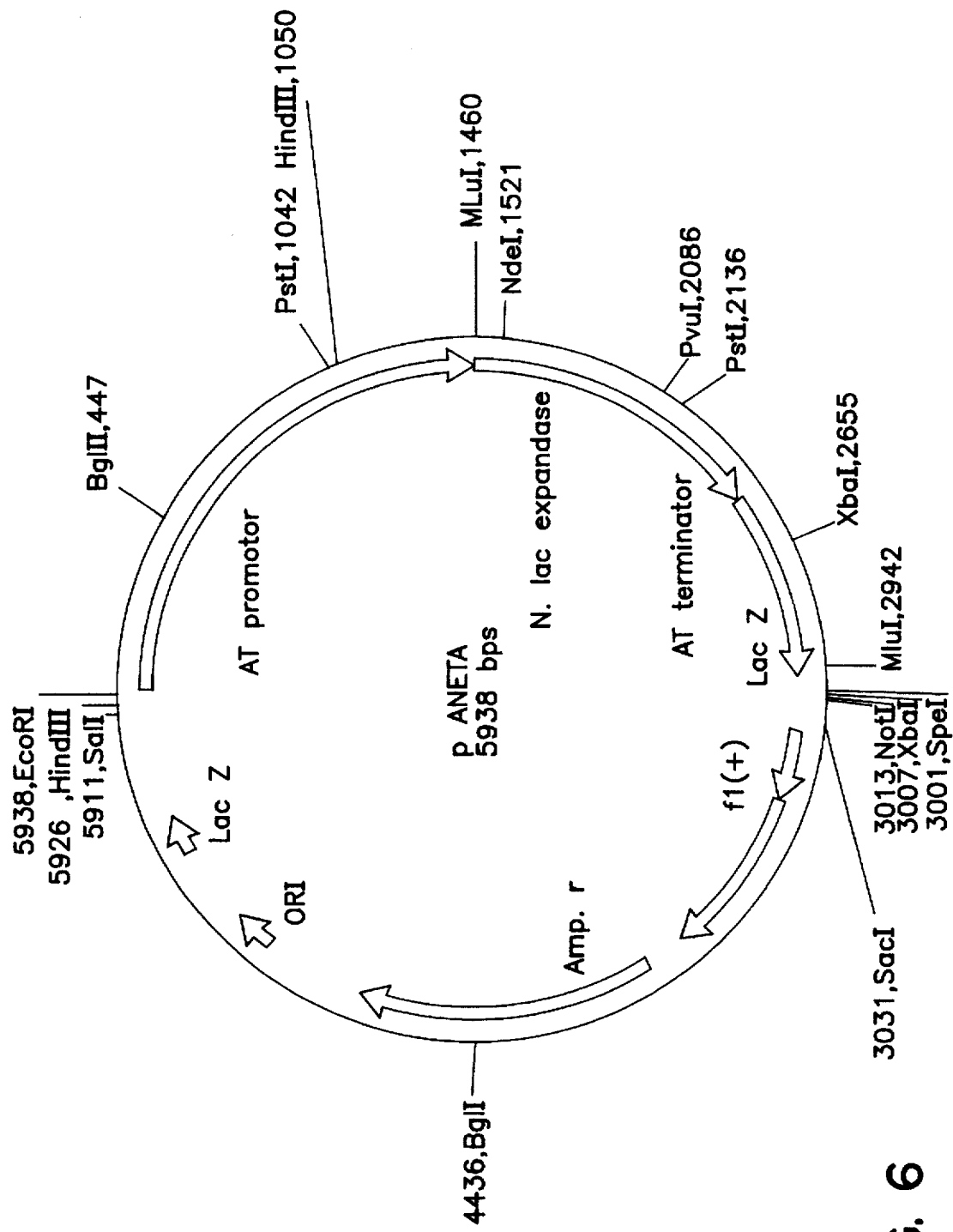
FIG. 6: A functional map of plasmid pANETA.
Figure 7:
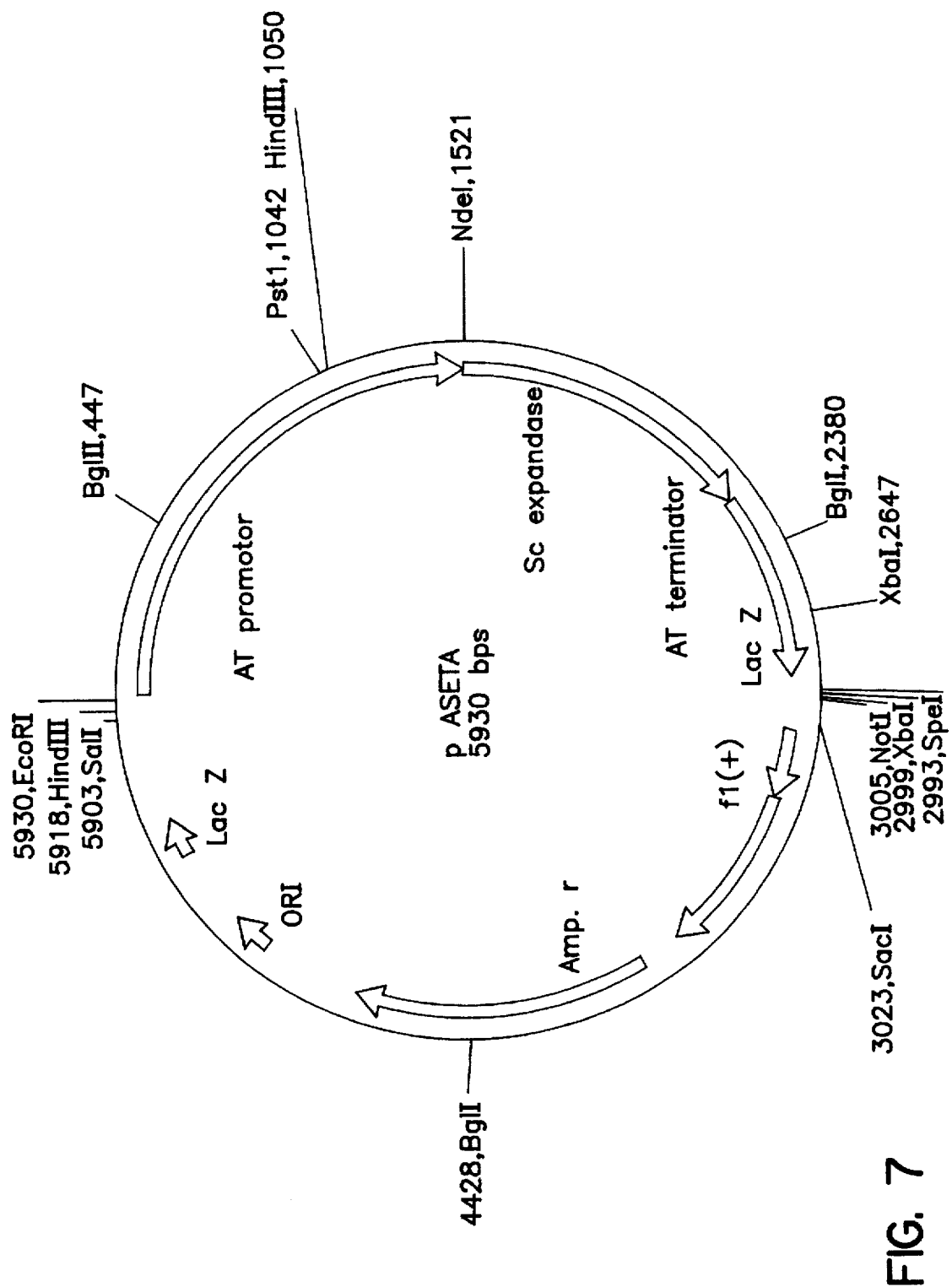
FIG. 7: A functional map of plasmid pASETA.

Transformants were grown and their plasmids were isolated and characterized by restriction fragment analysis and finally DNA sequence analysis. Thus the desired constructs were obtained, viz. pANETA (FIG. 6), pANEWA, pASETA (FIG. 7) and pASEWA.

d. Transformation of P. chrysogenum

The Ca-PEG mediated protoplast transformation procedure is used.

Following the procedures described in Cantoral (vide supra), Gouka et al. (J. Biotechn., vide supra) and Gouka et al. (Appl. Microbiol. Biotechnol., vide supra) total plasmid or the purified cefE expression cassette (devoid of *E. coli* vector sequences) was used to transform strains of *P. chrysogenum* with the pyrG, niaD, facA or amdS (Beri et al., Curr. Genet. 11 (1987), 639–641) genes, respectively, as selection markers.

By using the homologous pyrG, niaD or facA selection markers in purified form, devoid of *E. coli* vector sequences, transformed *P. chrysogenum* strains were obtained which do not contain bacterial resistance genes.

European patent application No. 94201896.1 describes a method for obtaining selection marker gene free recombinant strains. This method was successfully used on *P. chrysogenum* transformants containing the *A. nidulans* amdS gene as a dominant selection marker.

The only elements of heterolegous naturethen, are the 0.9 kb cefE coding region, and, optionally, the 0.9 kb gpdA promoter region.

e. Analysis of transformants

*P. chrysogenum* transformants are purified by repeated cultivation on selective medium. Single stable colonies are used to prepare agar slants to produce spores and to screen for transformants containing the cefE expression cassette. Boiling a fragment of fresh mycelium from transformants on an agar plate was used to obtain enough template DNA to efficiently screen hundreds of transformants for the presence of the cefE gene using the PCR technique. (Seth, Fungel Genetics Conference, Asilomar (1991), abstract in Fungel Genetics Newsletter 38, 55.) By doing so efficiency of transformation was estimated.

Screening of transformants was also done using a bioassay. Transformants were grown on agar medium that contained the side-chain precursor of choice. E. coli ESS2231 was used as indicator bacterium in an agar overlay, that also contained Bacto penase to be able to discriminate between penicillin and cephalosporin production according to methods well known in the art and described for example in Guttierez et al., Mol. Gen. Genet. 225 (1991), 56–64).

Spores are used to inoculate P. chrysogenum culture medium as described in section d. After 72 hours of cultivation (at 25° C.) chromosomal DNA is isolated from the mycelium. The DNA is digested with a restriction enzyme with a 6 bp recognition sequence like EcoRI or PstI.

The DNA fragments are separated by agerose gel electrophoresis and blotted onto Gene screen nylon membranes (New England Nuclear). The Southern blots are hybridized with the $^{32}$p labelled PCR 2 product as a probe for cefE gene sequences. $^{32}$p labelling of purified PCR 2 product is achieved by random priming labelling in the presence of $\alpha^{32}$P dCTP by using a commercial labelling kit (Boehringer Mannheim)

Transformants containing the cefE coding sequence are tested for expression of the cefE gene product, here referred to as expandase activity.

Selected transformants are cultivated in penicillin production medium (see Example 2).

In a time-course experiment, mycelium samples are taken after 48, 72 and 96 hours of fermentation. Mycelial extracts are prepared and expandase activity is determined in crude extracts essentially as described in Rollins et al., Can. J. Microbiol. 34 (1988), 1196–1202. Transformants with expandase activity are tested for acyltransferase activity as well by the methods described in Alvarez et al., Antimicrob. Agent Chem. 31 (1987), 1675–1682).

From these analyses transformants with different levels of acyltransferase and expandase enzymetic activities are selected for fermentative production of 7-ADCA derivatives.

Example 2

Fermentative production of 2-(carboxyethylthio) acetyl- and 3-(carboxymethylthio)propionyl-7-ADCA and isolation of the same P. chrysogenum strain Wisconsin 54–1255 (ATCC 28089) is transformed with one of the DNA constructs as described in Example 1 and inoculated at 2 * 10$^6$ conidia/ml into a seed medium consisting of (g/l): glucose, 30; $(NH_4)_2SO_4$, 10; $KH_2PO_4$, 10; trace element solution I ($MgSO_4.7H_2O$, 25; $FeSO_4.7H_2O$, 10; $CuSO_4.5H_2O$, 0.5; $ZnSO_4.7H_2O$, 2; $Na_2SO_4$, 50; $MnSO_4.H_2O$, 2; $CaCl_2.2H_2O$, 5), 10 (ml/l) (pH before sterilization 6.5).

The seed culture is incubated for 48–72 hours at 25°–30° C. and subsequently used to inoculate 10–20 volumes of a production medium containing (g/l) lactose, 80; maltose, 20; $CaSO_4$, 4; urea, 3; $MgSO_4.7H_2O$, 2; $KH_2PO_4$, 7; NaCl, 0.5; $(NH_4)_2SO_4$, 6; $FeSO_4.7H_2O$, 0.1; 3'-carboxymethylthiopropionic acid, 5; trace element solution II ($CuSO_4.5H_2O$, 0.5; $ZnSO_4.7H_2O$, 2; $MnSO_4.H_2O$, 2; $Na_2SO_4$, 50), 10 (ml/l) (pH before sterilization 5.5–6.0). The incubation is then continued for another 96–120 hours.

At the end of the production fermentation the mycelium is removed by centrifugation or filtration and 2-(carboxyethylthio)-acetyl- and 3-(carboxymethylthio) propionyl-7-ADCA are analyzed by high performance liquid chromatography (HPLC) on a reversed-phase column. The HPLC apparatus used is a Beckman System Gold, consisting of a model 126 programmable solvent system, a model 507 autosampler, a model 168 diode-array detector and System Gold data system (5.10). As the stationary phase two (2) Chromspher C18 cartridge columns (100×3 mm, Chrompack) in series are used. The mobile phase consists of a linear gradient from 100% 0.07M phosphate buffer pH 4.8 to 25% acetonitrile and 75% phosphate buffer pH 4.8 in 15 minutes at a flow rate of 0.5 ml/min. The production of 2-(carboxyethylthio) acetyl- and 3- (carboxymethyl-thio) propionyl-7-ADCA is quantitated at 260 nm using synthetic 2- (carboxyethylthio) acetyl- and 3- (carboxymethylthio) propionyl-7-ADCA as reference substances.

The peak identity is confirmed by comparison of the on-line UV and NMR spectra.

After filtering of the broth about 0.1 volume of 1-butanol is added to the filtrate. The pH value is adjusted to 2 with diluted hydrochloric acid and the mixture is stirred for 5 minutes at room temperature. After separation, the organic layer is either evaporated and further used in the chemical deacylation (example 3) or back-extracted with 0.33 volume of water of pH 8 and used further in the enzymatic deacylation (examples 4 and 5).

Example 3

Deacylation of 2-(carboxyethylthio)acetyl- and 3-(carboxymethylthio)propionyl-7-ADCA To a mixture of 3 g (8 mmoles) 2-(carboxyethylthio) acetyl-and 3-(carboxymethylthio)propionyl-7-ADCA, 3.5 ml (36 moles) of N,N-dimethylaniline, 13 ml of methylene chloride, and 2.6 ml (21 moles) of trimethylchlorosilane is added at ambient temperature. After stirring for 30 minutes the reaction mixture is cooled to about −50° C. and 1.8 g (8.5 mmoles) of phosphorus pentachloride is added all at once. The temperature is maintained at −40° C. for two hours and subsequently the reaction mixture is cooled to −65° C. It is then treated with 12 ml (137 mmoles) of isobutanol at such a rate that the temperature does not rise above −40° C. After additional stirring for two hours, the solution is poured in 15 ml of water, and 5 ml of 4.5N ammonia is added immediately afterwards. The pH is adjusted to 4 by slow addition of solid ammonium bicarbonate. After cooling to 5° C. the mixture is filtered, the crystalline 7-ADCA is washed with 5 ml of aqueous acetone (1:1) and isolated.

Example 4

Enzymetic deacylation of 2-(carboxyethylthio) acetyl- and 3-(carboxymethylthio)propionyl-7-ADCA using a mutant of Pseudomonas SY77 acylase The conversion of 2-(carboxyethylthio)acetyl-and 3-(carboxymethylthio)propionyl-7-ADCA is carried out in a single enzymatic step using a specific acylase which has been derived from Pseudomonas SY77 acylase via region directed mutagenesis. The construction and identification of the mutant Pseudomonas SY77 acylase with improved activity towards the 2-(carboxyethylthio)-acetyl- and 3-(carboxymethylthio)propionyl side chain has been described in EP-A-0453048. In the mutant the tyrosine at position 178 in the α-subunit of the Pseudomonas SY77 acylase has been replaced by histidine. The mutant acylase is produced in *E. coli*. Cells are harvested by centrifugation and resuspended in 10 mM phosphate buffer pH 7.4 containing 140 mMNaCl. Subsequently the cells are disrupted by sonification. After removing the cell debris the supernatants containing the acylase activity are collected. Further purification of the acylase is performed by a series of chromatographic steps: (1) ion-exchange chromatography on Q-sepharose fast-flow at pH 8.8; (2) hydrophobic interaction chromatography on Phenyl-Sepharose; and (3) gel-permeation chromatography on a Sephacryl S200HR column.

The purified acylase is immobilized onto particles consisting of a mixture of gelatin and chitosan. The particles are treated with glutaraldehyde just before addition of the enzyme.

The conversion of 2-(carboxyethylthio)acetyl-and 3-(carboxymethylthio)propionyl-7-ADCA is carried out in a stirred tank reactor. First the aqueous cephalosporin solution is added to the reactor. Subsequently the temperature of the solution is brought to 30° C. at constant stirring and the pH is fixed at 8 with potassium hydroxide. Then the immobilized enzyme is added and the conversion starts. During the conversion the pH in the reactor is recorded continuously and kept at 8. The 3'-carboxymethylthio propionic acid which is liberated during the reaction is titrated with KOH. The amount of KOH which is added is integrated and recorded on a flatbed recorder. The conversion is monitored by collecting samples from the reactor which are analyzed for 2-(carboxyethylthio)acetyt- and 3-(carboxymethylthio) propionyl-7-ADCA and 7-ADCA by HPLC as described in Example 2.

When the reaction is completed the immobilized enzyme is removed by filtration and the pH of the filtrate is brought to 1 while the filtrate comprises butyl acetate. The layers are separated and the pH of the aqueous phase which contains 7-ADCA is adjusted to 3. The crystalline 7-ADCA is then filtered off.

Example 5

Enzymatic deacylation of 2-(carboxyethylthio) acetyl- and 3-(carboxymethylthio)propionyl-7-ADCA using Pseudomonas SE83 acylase The conversion of2-(carboxyethylthio)acetyl-and 3-(carboxymethylthio)propionyl-7-ADCA is carried out as in example 4, however, under the application of Pseudomonas SE83 acytase as acylase, yielding the same result.

We claim:

1. A process for the preparation and recovery of 7-aminodesacetoxycephalosporanic acid (7-ADCA) by:
   a) transforming a *Penicillium chrysogenum* strain with an expandase gene, under the transcriptional and translational regulation of filamentous fungal expression signals;
   b) fermenting said strain in a culture medium and adding to said culture medium 3'-carboxymethylthiopropionic acid or a salt or ester thereof suitable to yield 2-(carboxyethylthio)acetyl- and 3-(carboxymethylthio)propionyl-6-aminopenicillanic acid (2-(carboxyethylthio)acetyl- and 3-(carboxymethylthio)propionyl-6-APA), which are in situ expanded to form 2-(carboxyethylthio)acetyl- and 3-(carboxymethylthio)propionyl-7-ADCA;
   c) recovering the 2-(carboxyethylthio)acetyl- and 3-(carboxymethylthio)propionyl-7-ADCA from the fermentation broth;
   d) deacylating said 2-(carboxyethylthio)acetyl- and 3-(carboxymethylthio)propionyl-7-ADCA; and
   e) recovering the crystalline 7-ADCA.

2. A process according to claim 1, wherein step (e) is a filtration step.

3. A process according to claim 1, wherein step (c) is a filtration step, and by extracting the broth filtrate with an organic solvent immiscible with water at a pH of lower than about 4.5 and back-extracting the same with water at a pH between 4 and 10.

4. A process according to claim 1 wherein the expandase gene is derived from *Streptomyces clavuligerus* or *Nocardia lactamdurans*.

* * * * *